(12) United States Patent
Sinoway et al.

(10) Patent No.: US 6,494,572 B1
(45) Date of Patent: Dec. 17, 2002

(54) EYEWEAR LENS DISPLAY KIT FOR SELECTING EYEWEAR LENSES FOR AN EYEWEAR FRAME

(75) Inventors: Tracy Sinoway, 404 E. 79th St., Apt. 15E, New York, NY (US) 10021; Stuart Freilich, Fairfield, CT (US)

(73) Assignee: Tracy Sinoway, New York, NY (US)

( * ) Notice: Subject to any disclaimer, the term of this patent is extended or adjusted under 35 U.S.C. 154(b) by 0 days.

(21) Appl. No.: 09/548,075

(22) Filed: Apr. 12, 2000

Related U.S. Application Data

(60) Provisional application No. 60/129,176, filed on Apr. 14, 1999.

(51) Int. Cl.[7] .................................................. G02C 9/00
(52) U.S. Cl. ........................................... 351/47; 351/57
(58) Field of Search ............................. 351/47, 48, 57, 351/58, 59, 41, 44

(56) References Cited

U.S. PATENT DOCUMENTS

| | | |
|---|---|---|
| 2,872,843 A | 2/1959 | Kono |
| 3,531,188 A | 9/1970 | Leblanc et al. |
| 4,029,402 A | 6/1977 | Noble |
| 4,247,178 A | 1/1981 | Cook |
| 4,561,739 A | 12/1985 | Okazaki |
| 5,123,724 A * | 6/1992 | Salk .............................. 351/57 |
| 5,488,439 A | 1/1996 | Weltmann |
| 6,007,197 A * | 12/1999 | Locatelli ...................... 351/47 |

\* cited by examiner

*Primary Examiner*—Hung Xuan Dang
(74) *Attorney, Agent, or Firm*—Gottlieb, Rackman & Reisman, P.C.

(57) ABSTRACT

An improved eyewear lens display system or kit is provided. The kit includes a plurality of clip assemblies. Each assembly includes a clip member that may be selectively attached to one of the lens holders of a pair of eyewear frames. A specific lens element is fixed to the clip member such that the lens element may be located along the lens receiving area of the frame when the clip member is attached to the frame's lens holder.

14 Claims, 3 Drawing Sheets

EYEWEAR LENS DISPLAY KIT FOR SELECTING EYEWEAR LENSES FOR AN EYEWEAR FRAME

This application claims the benefit of provisional application 60/129,176 filed Apr. 14, 1999.

BACKGROUND OF THE INVENTION

This invention relates to an eyewear lens display system, and more particularly, to a lens display system which enables the eyewear consumer to view his or herself with the exact coating, color or prescription that has been selected prior to purchase.

Currently, consumers try on eyewear frames by holding up a single lens in front of the frame in order to imagine what the eyewear frame would look like with a particular coating or tint color applied to the lenses. The disadvantage with this method is that it utilizes lenses of a very large size, which typically blocks the viewing of the entire frame.

In addition, most optical stores are looking for creative ways to display various tints and coatings that are to be applied to eyewear lenses. In a recently issued magazine, opticians were interviewed regarding how they try to demonstrate different coatings to the consumer. One optician utilizes a book of different colors which they show to the consumer. Other stores demonstrate different colors on a carousel from which a particular color is chosen. The problem with both of these systems is that the consumer is not able to evaluate how the lens color will look on a particular type of frame.

Accordingly, it is desirable to provide a eyewear lens display system which overcomes the above disadvantages.

SUMMARY OF THE INVENTION

Generally speaking, in accordance with the invention, an improved eyewear lens display system or kit is provided. The kit includes a plurality of clip assemblies. Each assembly includes a clip member that may be selectively attached to one of the lens holders of a pair of eyewear frames. A specific lens element is fixed to the clip member such that the lens element may be located along the lens receiving area of the frame when the clip member is attached to the frame's lens holder.

Significantly, each lens element has a unique coating, tint or other light transmissive or light reflective feature. As a result, the consumer is able to select a clip assembly from the kit with a specific tint, coating or other feature in order to see how a lens with that feature will appear in conjunction with a specific eyewear frame style.

The inventive system, as can be appreciated, enables the consumer to view the tint or coating of choice on the actual frame which is to be purchased. Each lens display kit will include a plurality of clip assemblies, some of which include lenses having different color tints, and some of which have lenses with a specialty coatings such as anti-reflective, mirrored, polarized and transition.

Optionally, the system will also include a certain number of clip assemblies with lenses having various types of visual prescriptions. For the customer who requires prescription lenses, the appropriate clip assembly for a prescription lens is chosen and attached along one of the lens holders. Then, a clip assembly having a specified lens coating or tint is chosen and attached to the other lens holder so that the prescription eyewearer can accurately see the coating or tint in combination with the eyewear frame.

Accordingly, it is an object of the invention to provide an improved eyewear lens display system.

Still another object of the invention to provide an improved eyewear lens display system which enables the eyewear consumer to view his or herself in a frame with a lens coating or tint that is desired.

Another object of the invention is to provide an improved eyewear lens display system which facilitates an optical salesperson in accurately showing the consumer the many different specialty tints and coatings that are available.

Yet a further object of the invention is to provide an improved eyewear lens display system which enables a consumer to use a prescription lens in order to accurately view his or herself with a particular lens tint or coating.

Still other objects and advantages of the invention will in part be obvious and will in part be apparent from the following description.

The inventive system has the features of construction and combination of elements that are described in the description set forth hereinbelow.

BRIEF DESCRIPTION OF THE DRAWINGS

For a fuller understanding of the invention, reference is made to the following description, taken in connection with the accompanying drawings, in which.

DETAILED DESCRIPTION OF THE PREFERRED EMBODIMENT

Figure 1:
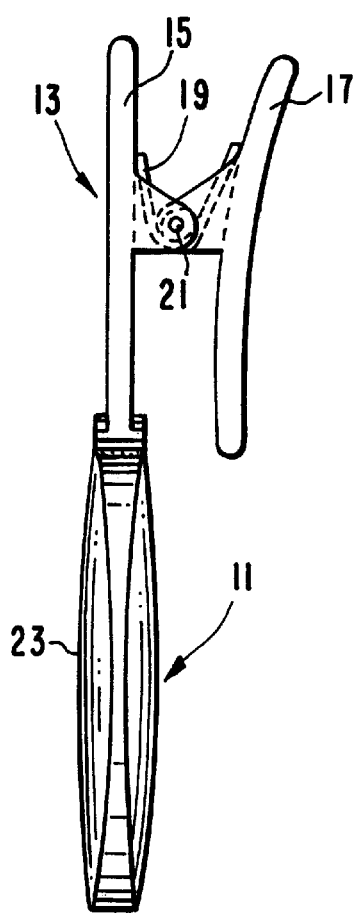
FIG. 1 is a side elevational view of a clip assembly of the inventive eyewear system.
Figure 2:
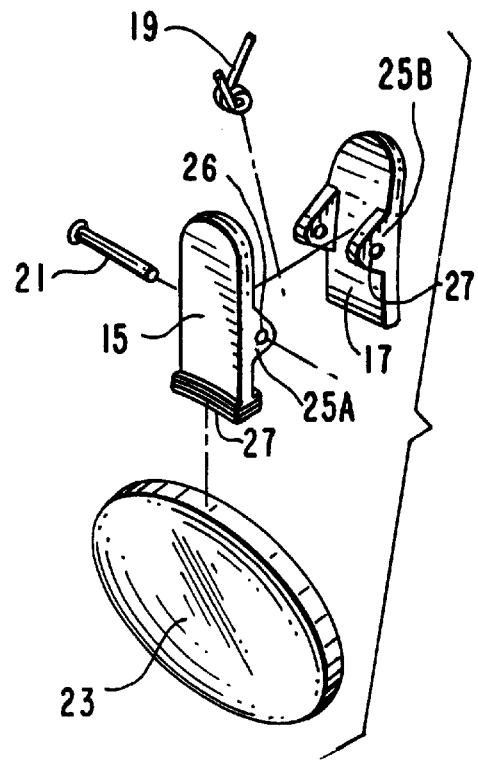
FIG. 2 is an exploded perspective view showing the various elements of the clip assembly depicted in FIG. 1.

Referring first to FIGS. 1 and 2, a clip assembly made in accordance with the inventive eyewear lens display system is generally indicated at 11. Clip assembly 11 includes a clip 13 and an attached lens 23 of standard size in the art. Clip 13 comprises a clip front 15 and a clip back 17. Clip front 13 includes a pair of bracket elements 25A having holes 26 and clip back includes a pair of bracket elements 25B having holes 27. In assembly, holes 26 and 27 of bracket elements 25A and 25B respectively are aligned (see FIG. 1) such that a pivot pin 21 passes therethrough, thereby engaging bracket elements 25A and 25B. Pivot pin 21 has a spring 19 wrapped thereabout to facilitate the clipping action of clip 13, as described later on.

As shown in FIG. 2, clip front 15 has a base 27 which is fixed along the edge of lens 23 (see FIG. 2). This attachment is achieved by gluing or other conventional adhesive mechanism.

Significantly, lens 23 has a specific tint or coating applied thereto. The tint is selected from six different colored tints, namely brown, gray, pink, green, blue and yellow. If a coating is applied, it may be selected from mirrored, polarized, transition and anti-reflective. These types of tints or coatings are well known in the art.

Figure 3:
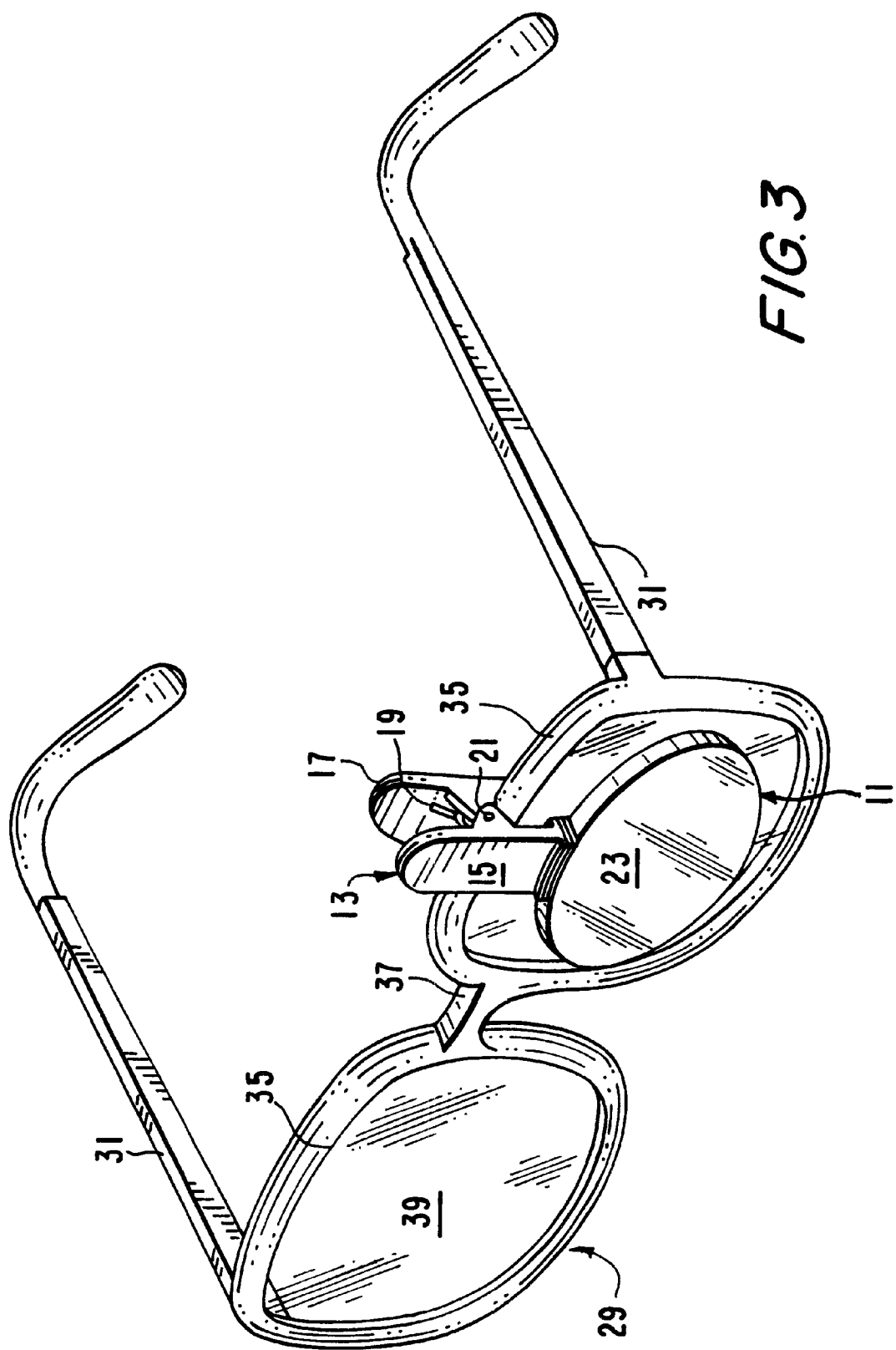
FIG. 3 is a perspective view of an eyewear frame having the inventive clip assembly mounted along one of the frame's lens holders.

Referring now to FIG. 3, the inventive clip assembly is shown used in conjunction with a conventional eyewear frame 29. Frame 29 includes a pair of lens holders 35, a connecting nosepiece 37, and a pair of earpieces 31, all as well known in the art. Each of the lens holders 35 defines a lens receiving area 39 therewithin in which a customized lens may be fixedly received. Optionally, lens receiving area 39 of frame 29 may include a non-prescription plastic lens element 24 (see FIG. 4) for try-on purposes.

As shown in FIG. 3, clip assembly 11 may be mounted to frame 29 by attaching clip 13 to the upper portion of one of lens holders 35. In this condition, the corresponding lens 23 of clip 13 is disposed along lens receiving area 39. Therefore, a consumer can try on frame 29 to see whether the tint or coating which was previously applied to lens 23 is desirable. If not desirable, the consumer or the optical salesperson can disconnect clip 13 from lens holder 33 and replace it with a clip 13 having a different tint or coating, to see if that tint or coating is more desirable.

Figure 4:
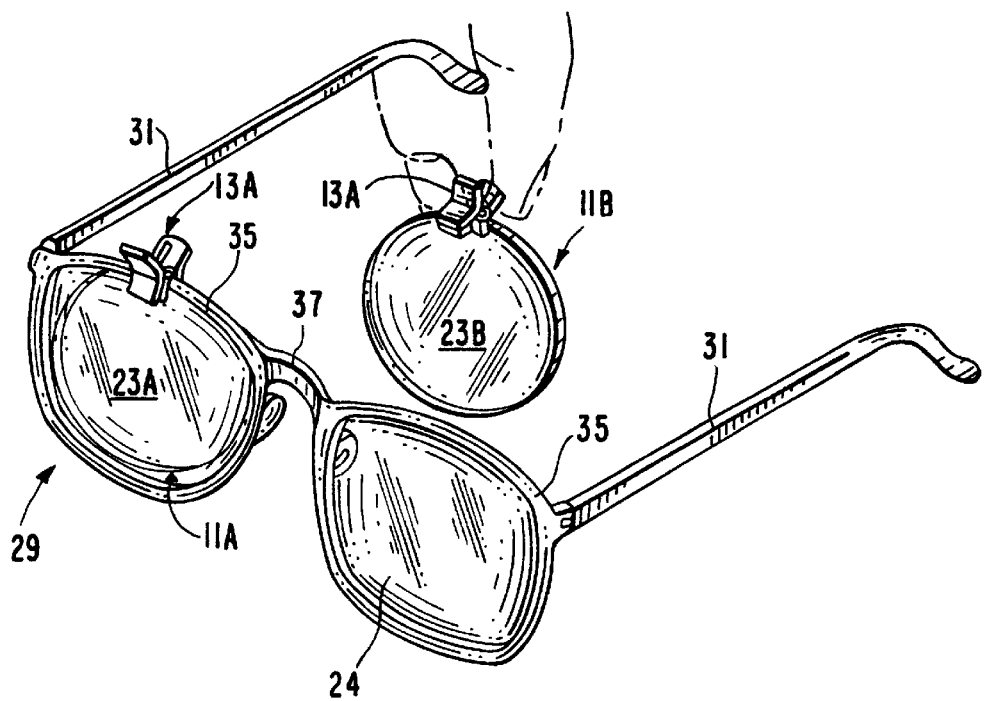
FIG. 4 is a perspective view of the eyewear frame with one clip assembly mounted to one of the frame's lens holders and a second about to be connected to the other lens holder.

Optionally, as shown in FIG. 4, a clip assembly 11A having a specific prescription lens 23A fixed to clip 13A is attached to one of lens holders 35. A second clip assembly 11B having a clip 13B and an attached lens 23B with a specific tint or coating is connected to the other lens holder 35; in this manner, a customer is able to view themselves through the prescription lens 23A in order to see if the tint or coating applied to lens 23B is what is desired. It is noted that clips 23A and B shown in FIG. 4 are slightly different in structure from the structure of clip 23 shown in FIGS. 1–3 but otherwise function in virtually the identical manner.

Figure 5:
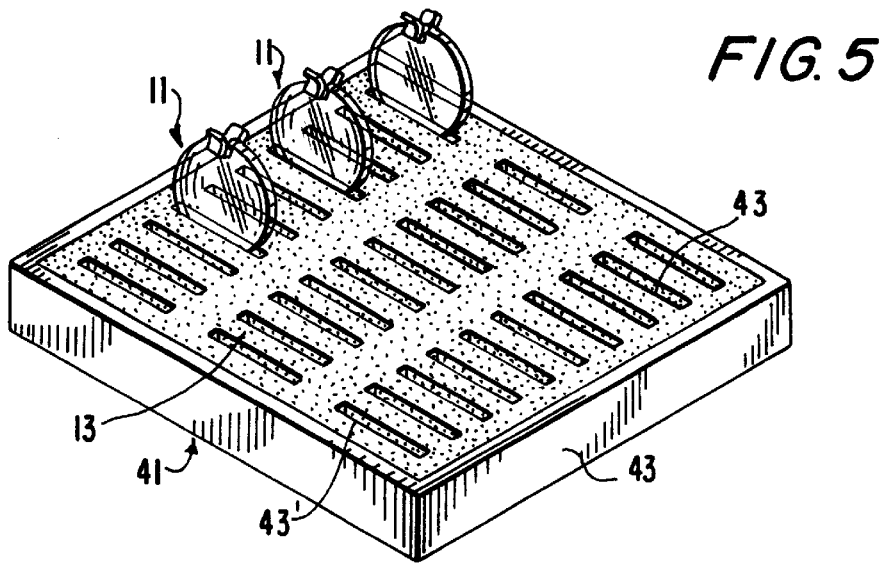
FIG. 5 is a perspective view of a kit containing a plurality of clip assemblies of the invention in which each clip assembly has a lens element with a different tint or coating.

In FIG. 5, a kit 41 for carrying and storing a plurality of different clip assemblies 11 of the inventive eyewear lens display system is shown. Kit 41 comprises a display box 43 having a series of slots 43 designed for receiving a plurality of clip assemblies 11—lens 23 of each assembly 11 is preferably of the same size and shape. This kit may be supplied to opticians and other optical salespeople so they have ready access to a plurality of inventive clip assemblies having various coatings, tints and prescriptions.

It will thus be seen that the objects set forth above, among those made apparent from the preceding description, are efficiently attained, and certain changes may be made in designing the inventive eyewear lens display system, and in using it, without departing from the spirit and scope of the invention.

It is further understood that the invention is defined in claims recited hereinbelow.

What is claimed is:

1. An eyewear lens display system comprising:
   a plurality of different eyewear frames, each of said frames including a pair of lens receiving areas having a unique shape and size as compared to that of said pair of lens receiving areas of any other of said frames;
   a plurality of universal clip assemblies, each said clip assembly comprising a single clip member for selective attachment to any of said frames, and a single lens element fixed to said clip member such that said lens element is disposable along at least a portion of either one of said lens receiving areas of said any of said frames when said clip member is selectively attached thereto;
   wherein said lens element of each of said plurality of clip assemblies has a unique light transmissive or light reflective feature that is different than that of the lens element of another of said clip assemblies.

2. The system of claim 1, wherein said feature is selected from the group consisting of a tinted lens, a mirrored lens, a polarized lens, a transition lens and an anti-reflective lens.

3. The system of claim 1, wherein said tinted lens is tinted from colors selected from the group consisting of brown, gray, pink, green, blue and yellow.

4. The system of claim 1, wherein said clip element has a front clip wing and a back clip wing.

5. The assembly of claim 4, wherein one end of said front clip wing is fixed to said lens element.

6. The system of claim 1, wherein said clip member further includes a spring element to facilitate opening and closing said front and back clip wings.

7. The system of claim 1, wherein said clip member of each of said clip assemblies is selectively attachable to any of said eyewear frames such that said lens element is disposable at different heights along at least a portion of either one of said lens receiving areas of a selected eyewear frame.

8. An eyewear lens display kit for use in selecting an eyewear lens for a plurality of different eyewear frames each having two lens receiving areas of a unique shape and size, the kit comprising a plurality of universal clip assemblies, each said clip assembly comprising a single clip member designed for selective attachment to any of said eyewear frames; and a single lens element fixed to said clip member such that said lens element is disposable along at least a portion of either one of said lens receiving areas of said selected frame when said clip member is attached thereto;
   wherein said lens element of each of said plurality of clip assemblies has a unique light transmissive or light reflective feature that is different than that of the lens element of another of said clip assemblies.

9. The kit of claim 8, wherein said said feature is selected from a tinted lens, a mirrored lens, a polarized lens, a transition lens and an anti-reflective lens.

10. The kit of claim 9, wherein said tinted lens is tinted from colors selected from the group consisting of brown, gray, pink, green, blue and yellow.

11. The kit of claim 8, wherein said clip member further includes a spring element to facilitate opening and closing said front and back clip wings.

12. The kit of claim 8, wherein said clip member has a front clip wing and a back clip wing.

13. The kit of claim 8, wherein one end of said front clip wing is fixed to said lens element.

14. The kit of claim 8, wherein said clip member of each of said clip assemblies is selectively attachable to any of said eyewear frames such that said lens element is disposable at different heights along at least a portion of either one of said lens receiving areas of a selected eyewear frame.

* * * * *